(12) United States Patent
Abe

(10) Patent No.: US 6,537,269 B1
(45) Date of Patent: Mar. 25, 2003

(54) LASER TREATMENT APPARATUS

(75) Inventor: Hitoshi Abe, Okazaki (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 09/668,731

(22) Filed: Sep. 25, 2000

(30) Foreign Application Priority Data

Sep. 30, 1999 (JP) ............................................ 11-277795

(51) Int. Cl.⁷ ............................................... A61B 18/20
(52) U.S. Cl. ................................. 606/12; 606/4; 606/9; 606/11; 606/17
(58) Field of Search .......................... 606/4, 9, 11, 17, 606/12

(56) References Cited

U.S. PATENT DOCUMENTS

| | | | |
|---|---|---|---|
| 4,422,457 A | | 12/1983 | Hattori |
| 4,573,466 A | | 3/1986 | Simada et al. |
| 4,580,557 A | * | 4/1986 | Hertzmann ............ 219/121.61 |
| 5,166,513 A | | 11/1992 | Keenan et al. |
| 5,501,680 A | | 3/1996 | Kurtz et al. |
| 5,662,644 A | * | 9/1997 | Swor ............................ 606/10 |
| 6,030,376 A | * | 2/2000 | Arashima et al. ............. 606/12 |
| 6,066,129 A | * | 5/2000 | Larson ........................ 606/10 |
| 6,149,643 A | * | 11/2000 | Herekar et al. ................ 606/10 |

FOREIGN PATENT DOCUMENTS

EP 0 624 422 A2 11/1994

* cited by examiner

Primary Examiner—Lee Cohen
Assistant Examiner—Henry M. Johnson, III
(74) Attorney, Agent, or Firm—Oliff & Berridge, PLC

(57) ABSTRACT

A laser treatment apparatus for irradiating an affected part of a patient with a treatment laser beam to treat the affected part is disclosed. The apparatus includes a treatment beam irradiation part including an irradiation optical system for delivering the treatment laser beam to the affected part to irradiate it; an input part for inputting an instruction signal of irradiation of the treatment laser beam; a mode selection part for selecting one of an irradiation ready mode in which the irradiation of the treatment laser beam is enabled when the irradiation instruction signal is input with the input part and a standby mode in which the irradiation of the treatment laser beam is disabled even if the irradiation instruction signal is input; a detection part for detecting whether an operator is in a predetermined condition to enable the laser irradiation; and an irradiation control part for controlling the irradiation of the treatment laser beam in accordance with a selection result by the mode selection part, a detection result by the detection part, and a presence/absence of input of the irradiation instruction signal.

9 Claims, 5 Drawing Sheets

LASER TREATMENT APPARATUS

BACKGROUND OF THE INVENTION

1. Field of the Invention

The present invention relates to a laser treatment apparatus for irradiating an affected part of a patient with a treatment laser beam to treat the affected part.

2. Description of Related Art

As laser treatment apparatus, there are for example an ophthalmic photocoagulation apparatus, a plastic surgical device for removing blotches and wrinkles, and a depilation apparatus. These apparatus are configured to have two states; an irradiation preparation completion state in which irradiation of a treatment laser beam (hereinafter simply referred to as "laser irradiation") is enabled in response to a laser irradiation instruction signal (a trigger signal), which is referred to as a READY mode, and a wait state in which the laser irradiation is disabled even if the irradiation instruction signal is input, which is referred to as a STANDBY mode. The selection between the two modes is done with switches (keys) on a control panel of the apparatus. An operator, after confirming that the preparation for the laser irradiation is completed, operates an appropriate key to place the apparatus in the READY mode and starts the laser irradiation.

However, for example, when the operator leaves his position while the apparatus remains placed in the READY mode, a third party may accidentally or erroneously input the irradiation instruction signal, performing undesired laser irradiation. There may also be a case where the operator himself unintentionally performs the laser irradiation, for example, the operator inputs the irradiation instruction signal with a corresponding switch or key even though he is not observing the affected part or before the completion of the preparation for irradiation.

SUMMARY OF THE INVENTION

The present invention has been made in view of the above circumstances and has an object to overcome the above problems and to provide a laser treatment apparatus capable of preventing erroneous irradiation of a treatment laser beam.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser treatment apparatus for irradiating an affected part of a patient with a treatment laser beam to treat the affected part, the apparatus including: treatment beam irradiation means including an irradiation optical system for delivering the treatment laser beam to the affected part to irradiate it; input means for inputting an instruction signal of irradiation of the treatment laser beam; mode selection means for selecting one of an irradiation ready mode in which the irradiation of the treatment laser beam is enabled when the irradiation instruction signal is input with the input means and a standby mode in which the irradiation of the treatment laser beam is disabled even if the irradiation instruction signal is input; detection means for detecting whether an operator is in a predetermined condition to enable the laser irradiation; and irradiation control means for controlling the irradiation of the treatment laser beam in accordance with a selection result by the mode selection means, a detection result by the detection means, and a presence/absence of input of the irradiation instruction signal.

In the laser treatment apparatus, preferably, only when the irradiation ready mode is selected with the mode selection means and besides the detection means detects that the operator is in the predetermined condition to enable the laser irradiation, the irradiation control means enables the irradiation of the treatment laser beam in response to the irradiation instruction signal input with the input means.

It is preferable that the laser treatment apparatus further includes observation means provided with eyepieces and an observation optical system for allowing the operator to observe the affected part, wherein the detection means is disposed in the eyepieces to detect whether the operator is in the predetermined condition to enable the laser irradiation based on whether a face of the operator is within a predetermined distance from the eyepieces.

Preferably, the laser treatment apparatus further includes a moving mechanism provided with a hand operated member for moving at least a part of the irradiation optical system with respect to the affected part, wherein the detection means is disposed in the hand operated member to detect whether the operator is in the predetermined condition to enable the laser irradiation based on whether the operator is holding the hand operated member.

Preferably, the laser treatment apparatus further includes a hand-piece in which at least a part of the irradiation optical system is disposed, wherein the detection means is disposed in the hand-piece to detect whether the operator is in the predetermined condition to enable the laser irradiation based on whether the operator is holding the hand-piece.

In the above laser treatment apparatus, the detection means preferably includes one of a photo-sensor, a touch-sensor, and a micro-switch.

In the laser treatment apparatus, preferably, the irradiation control means includes a shutter which is retractably inserted in an optical path of the irradiation optical system, a moving device for moving the shutter into or out of the optical path, and a control unit for controlling driving of the moving device.

In the laser treatment apparatus, preferably, the treatment beam irradiation means includes a laser source which emits the treatment laser beam, and the irradiation control means includes a control unit for controlling driving of the laser source.

It is preferable that the laser treatment apparatus further includes aiming beam irradiation means, provided with an aiming laser source which emits an aiming beam to be used for sighting the treatment laser beam on the affected part, for delivering the aiming beam emitted from the aiming laser source to the affected part to irradiate it; and light source control means for controlling the aiming laser source in accordance with the detection result by the detection means.

Preferably, the laser treatment apparatus further including illumination means, provided with an illumination light source which emits an illumination light, for illuminating an area including the affected part with the illumination light emitted from the illumination light source, and light source control means for controlling the illumination light source in accordance with the detection result by the detection means.

Preferably, the laser treatment apparatus further includes power source control means for controlling power supply to a whole or part of the apparatus in accordance with the detection result by the detection means.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

A detailed description of preferred embodiments of a laser treatment apparatus embodying the present invention will now be given referring to the accompanying drawings.

Figure 1:
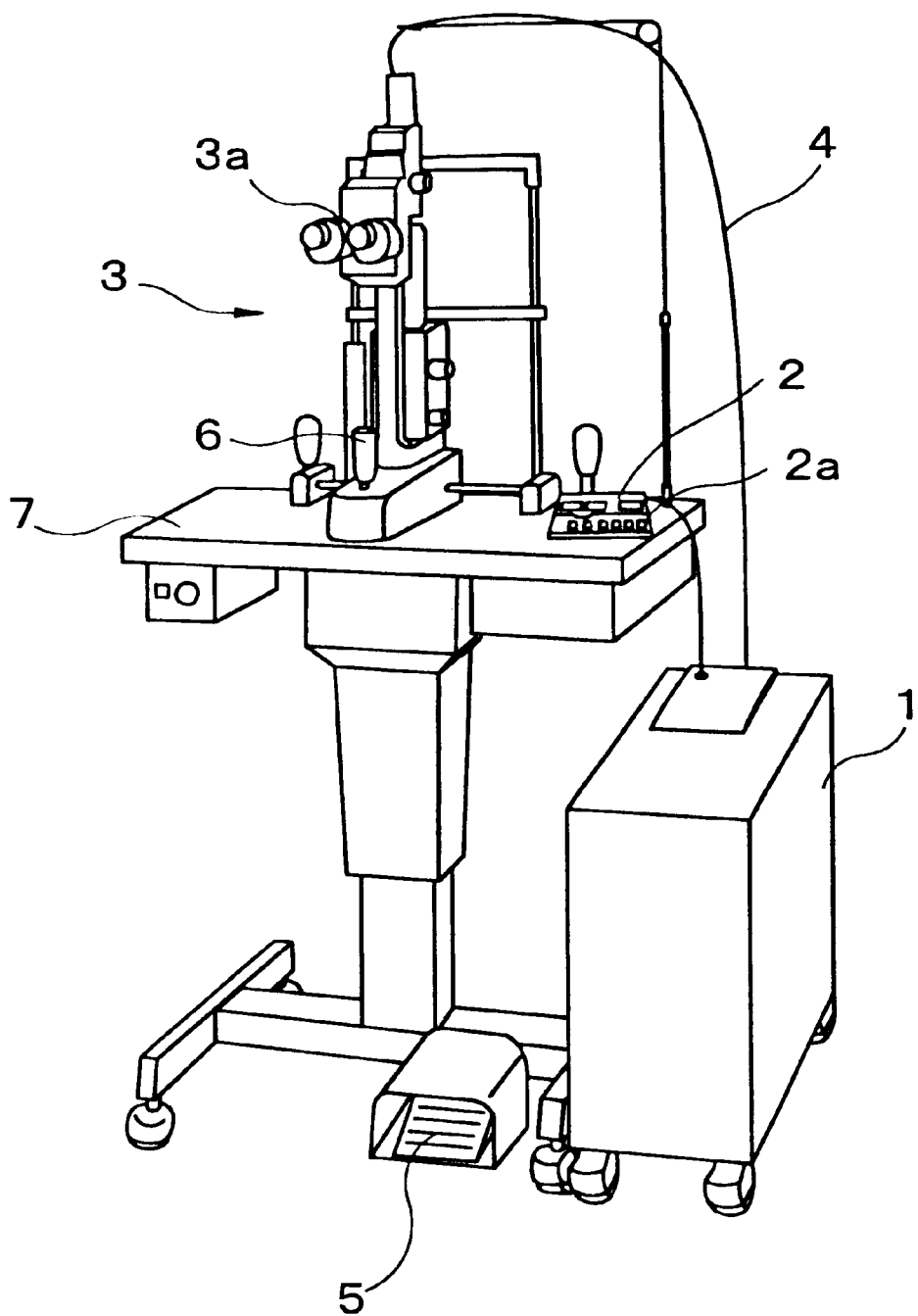
FIG. 1 is a drawing of a laser photocoagulation apparatus in a first embodiment according to the present invention.
Figure 2:
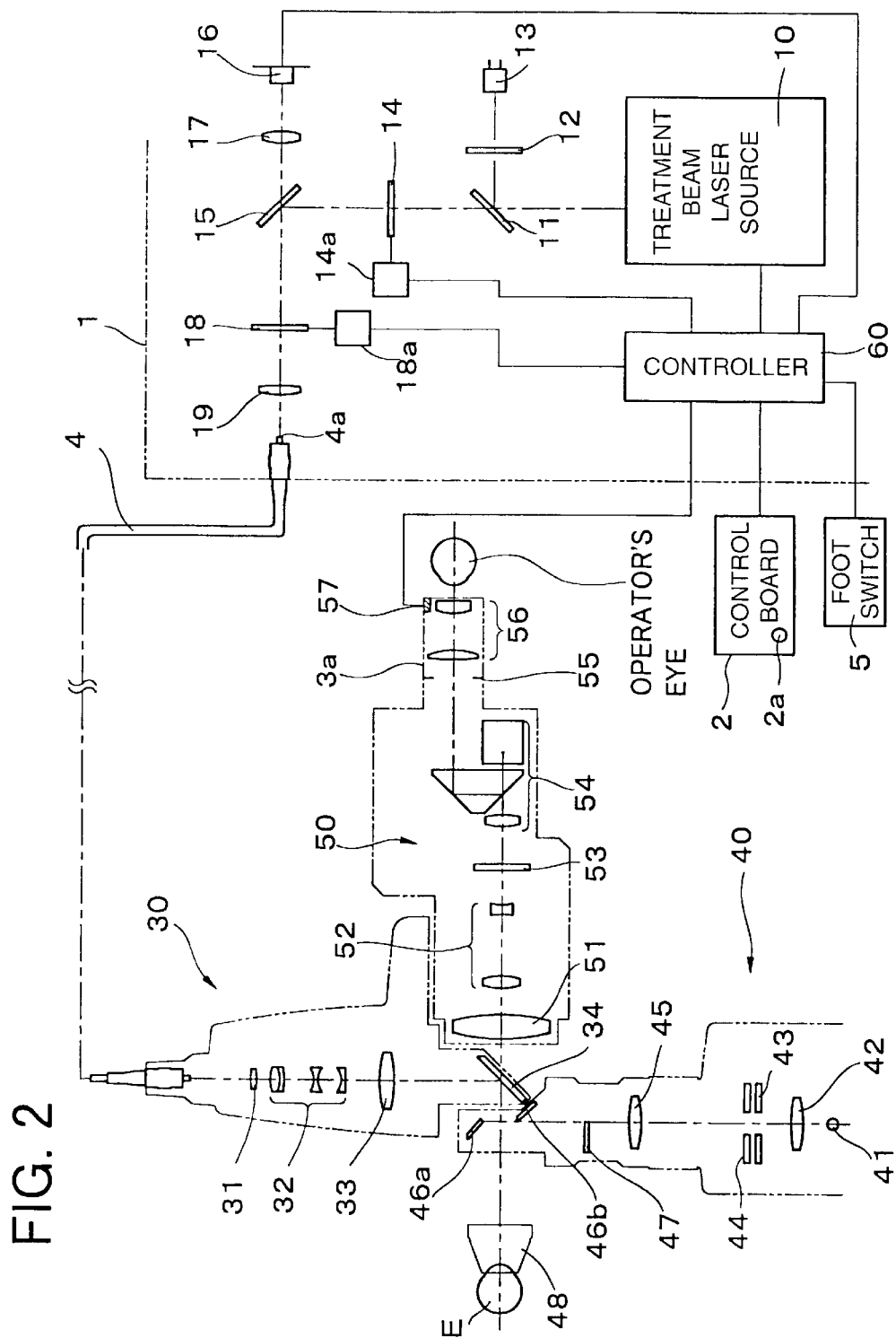
FIG. 2 is a schematic structural apparatus of an optical system and a control system of the laser photocoagulation apparatus.

In the first embodiment the present invention is applied to a laser photocoagulation apparatus used for ophthalmic treatment. FIG. 1 is a drawing of the laser photocoagulation apparatus in a first embodiment. FIG. 2 is a schematic structural view of an optical system and a control system of the apparatus.

Numeral 1 is a main unit of the apparatus. Numeral 2 is a control board used for inputting irradiation conditions such as light quantity and others of a treatment laser beam (hereinafter simply referred to as a treatment beam) and an aiming laser beam (hereinafter simply referred to as an aiming beam). The control board 2 is provided with a mode changing switch 2a for switching between a laser irradiation enabled state (a preparation completion state, or a READY mode) in which irradiation of the treatment beam (laser irradiation) is enabled and a laser irradiation disabled state (a wait state, or a STANDBY mode). Numeral 3 is a slit lamp delivery including binocular eyepieces 3a through which an operator can observe an eye E of a patient. The slit lamp delivery 3 is internally provided with an irradiation optical system 30, an illumination optical system 40, and an observation optical system 50.

Numeral 4 is an optical fiber cable for delivering the treatment beam and the aiming beam from the main unit 1 to the slit lamp delivery 3. Numeral 5 is a footswitch for generating a laser irradiation instruction signal (a trigger signal) when depressed by the operator. Numeral 6 is a joystick provided in a base part 3b of the slit lamp delivery 3. This joystick 6 is operated to move the slit lamp delivery 3 on a table of a base stand 7. The moving mechanism using the joystick 6 will be explained later.

Numeral 10 is a laser source which emits the treatment beam. In the present embodiment, an Nd:YAG laser capable of oscillating a fundamental wavelength of 1064 nm is used as the laser source 10 to generate a green light of 532 nm (linearly polarized light) which is double the fundamental wavelength. Numeral 11 is a beam splitter for transmitting most of the treatment beam emitted from the laser source 10, while reflecting a part thereof toward a diffusing plate 12. The reflected part of the treatment beam by the beam splitter 11 is incident to a power sensor 13 through the diffusing plate 12. The power sensor 13 detects the output power of the treatment beam emitted from the laser source 10.

Numeral 14 is a first safety shutter retractably disposed in an optical path of the treatment beam emitted from the laser source 10. When the footswitch 5 is depressed, the controller 60 receives the irradiation instruction signal from the footswitch 5 and drives a shutter moving unit 14a to retract the first shutter 14 from the optical path, thereby allowing passage of the treatment beam. In a case for example of occurrence of an abnormal event, on the other hand, the first shutter 14 is inserted in the optical path to intercept the treatment beam. The details thereof will be mentioned later.

Numeral 16 is a laser source which emits the aiming beam. In the present embodiment, the laser source is a laser diode capable of emitting a red light having a wavelength of 630 nm. The aiming beam emitted from the laser source 16 passes through a collimator lens 17 and it is made coaxial with the treatment beam by a dichroic mirror 15.

Numeral 18 is a second safety shutter, which is inserted in or retracted from the optical path by a shutter moving unit 18a. Numeral 19 is a condensing lens, which condenses the laser beams into an entrance end 4a of the fiber 4. The laser beams are then delivered through the fiber 4 into the irradiation optical system 30 of the slit lamp delivery 3.

The irradiation optical system 30 is structured of a collimator lens 31, a group of variable magnification lenses 32, an objective lens 33, and a driven mirror 34. The variable magnification lenses 32 are moved along the optical axis with the turn of a knob not shown to thereby change each spot diameter of the laser beams. The driven mirror 34 can freely change its reflecting angle with the control of a manipulator not shown by the operator.

The illumination optical system 40 is provided with a light source 41 which emits a visible illumination light, a condensing lens 42, a variable circular aperture 43, a variable slit plate 44, a projective lens 45, splitting mirrors 46a and 46b, and a correcting lens 47. The aperture 43 and the slit plate 44 are used for determining the height and width of the illumination light to form luminous flux in a slit form. Numeral 48 is a contact lens for laser treatment, which is placed on the eye E of a patient.

The observation optical system 50 is constructed of an objective lens 51 used in common between a right and left observation optical paths and two sets each including a group of variable magnification lenses 52, a protective filter 53 for protecting the eyes of the operator, a group of erect prisms 54, a field diaphragm 55, and a group of eyepiece lenses 56. Each set of the components 52–56 is disposed on the right and left optical paths respectively. The operator can observe the eye E through the thus constructed observation optical system 50 by looking through the binocular eyepieces 3a.

At least one of the binocular eyepieces 3a is provided with a photo-sensor 57 for detecting whether the operator is observing the eye E, namely, whether the operator is in a predetermined condition to enable the laser irradiation. The photo-sensor 57 is structured of an infrared emitter and a photoreceptor. When the eyes or face of the operator come near within a predetermined distance from the photo-sensor 57, an infrared light emitted from the emitter is reflected by the operator's face and received by the photoreceptor, generating a detection signal representing that the operator is observing the eye E to be treated. It is to be noted that the photo-sensor 57 may be of a type of detecting light quantity.

The controller 60 controls the laser sources 10 and 16, the shutter moving units 14a and 18a, the light source 41 and others in accordance with the irradiation conditions and mode set with the control board 2, the presence/absence of the irradiation instruction signal from the footswitch 5, the presence/absence of the detection signal from the photo-sensor 57, and others.

Figure 5:
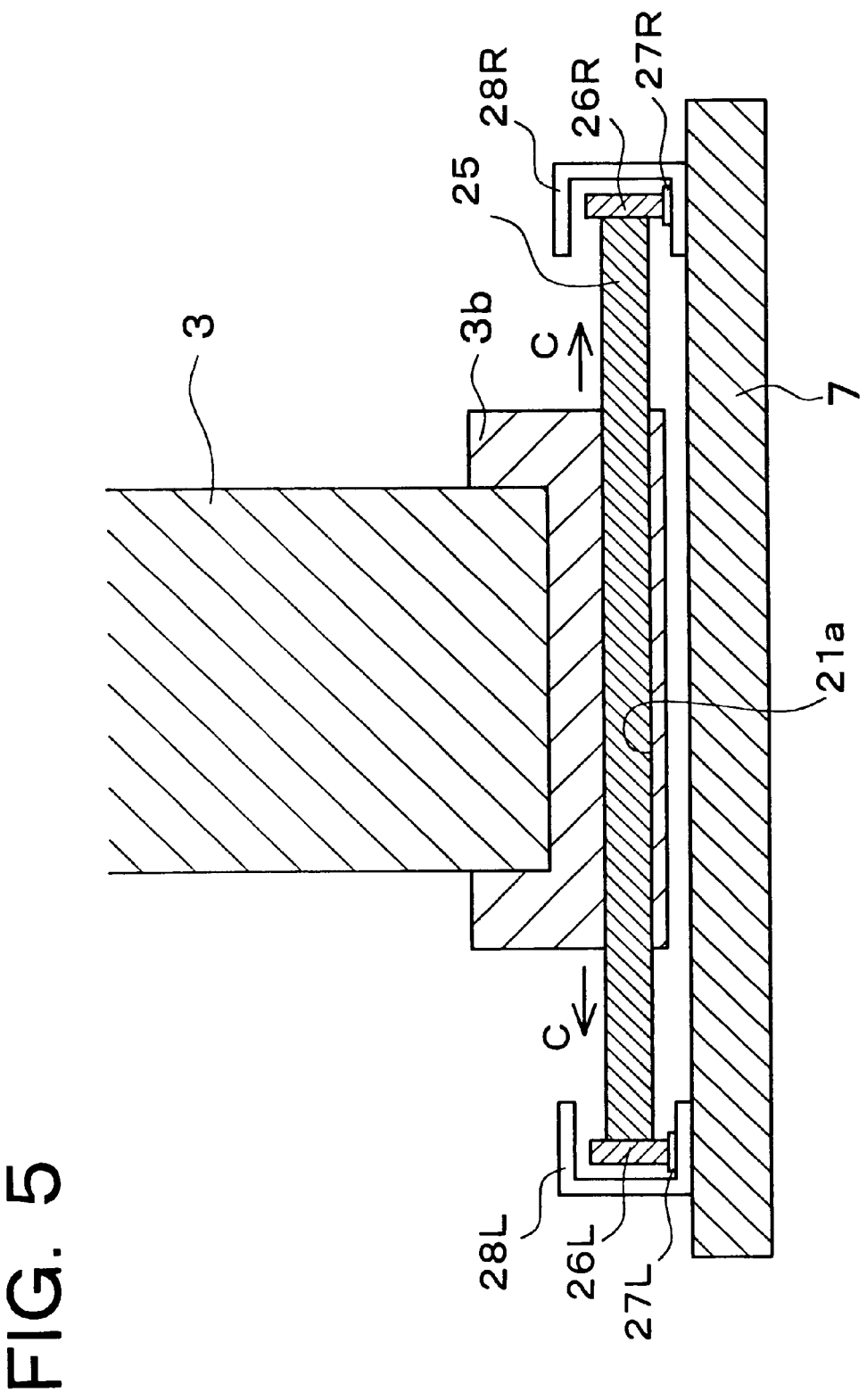
FIG. 5 is a schematic sectional view of a moving mechanism of a slit lamp delivery in the first embodiment according to the present invention.

FIG. 5 is a schematic sectional view of the mechanism of moving the slit lamp delivery 3. An axle 25 is rotatably inserted in a through hole 21a of the base part 3b of the slit lamp delivery 3 so that the base part 3b may be slid in an axial direction of the axle 25. The sliding of the base part 3b and the rotating of the axle 25 are facilitated by means of a bearing not shown. Gears 26R, 26L are attached to both ends of the axle 25 and engaged with a pair of rails 27R, 27L. These rails 27R, 27L are formed with rack teeth and laid on the table of the base stand 7 in parallel with each other and in an orthogonal direction to the drawing sheet of FIG. 5. With such the configuration, when the joystick 6 is operated to exert force on the base part 3b in a forward/backward direction (i.e., a lengthwise direction of the rails 27R, 27L), the gears 26R, 26L fixed to the axle 25 are rotated in engagement with the rails 27R, 27L, making it possible to move the base part 3b in the forward/backward direction. Alternatively, when the joystick 6 is operated to exert force on the base part 3b in a right/left direction (i.e., the axial direction of the axle 25), the base part 3b is slid on the axle 25 in the direction indicated by an arrow C in FIG. 5. Accordingly, the above moving mechanism enables movement of the slit lamp delivery 3 mounted on the base part 3b in the frontward/backward and right/left directions on the table of the base stand 7. It is to be noted that the joystick 6 is provided with a supporting mechanism (not shown) contacting the surface of the table for horizontally movably supporting the main unit 1 on the table. Reference numerals 28R, 28L are covers that cover the rails 27R, 27L along their entire lengths for protecting the gears 26R, 26L put on the rails 27R, 27L.

Operation of the laser photocoagulation apparatus having the above configuration will be explained below.

When the operator or assistant turns on the power of apparatus, the controller 60 runs self-check (self-diagnosis) of the apparatus and then starts up, establishing the STANDBY mode. Then, the operator observes the fundus of the eye E through the eyepieces 3a (the observation optical system 50), the eye E being illuminated with an illumination light from the illumination optical system 40. The operator operates the control board 2 to emit the aiming beam. Upon receipt of an instruction of the aiming beam irradiation, the controller 60 causes the laser source 16 to emit the aiming beam and, simultaneously, drives the shutter moving unit 18a to move the second shutter 18 out of the optical path. While observing the aiming beam irradiated to the eye fundus, the operator also operates the joystick 6 and a manipulator not shown to perform sighting (alignment) with respect to the affected part. With various switches on the control board 2, the operator inputs the irradiation conditions such as the irradiation power and irradiation time of the treatment beam. Alternatively, these irradiation conditions may be set in advance. After completion of preparation for the laser irradiation, the operator presses the switch 2a to place the apparatus in the READY mode.

At this time, if the operator is looking through the eyepieces 3a, the photo-sensor 57 detects that the operator is observing (in a predetermined condition to enable the laser irradiation), generating a detection signal to the controller 60. In the READY mode, when the controller 60 continuously receives the detection signal from the photo-sensor 57 and besides receives the irradiation instruction signal from the footswitch 5, it operates to retract the first shutter 14 from the optical path, enabling the laser irradiation. The treatment beam is delivered through the laser delivery optical system provided in the main unit 1, the optical fiber 4, and the irradiation optical system 30 to the eye E, thus irradiating the affected part of the eye E.

If the operator takes his eyes off the eyepieces 3a, on the other hand, the controller 60 receives no detection signal from the photo-sensor 57. Therefore, the controller 60 determines that the operator is not observing (in the predetermined condition to enable the laser irradiation). Without the detection signal from the photo-sensor 57 in the READY mode, the controller 60 disables the laser irradiation by retaining the first shutter 14 in the optical path even if the irradiation instruction signal is input from the footswitch 5. In other words, the irradiation instruction signal from the footswitch 5 becomes effective only if the operator is looking through the eyepieces 3a. Accordingly, when the operator's eyes (face) are apart from the eyepieces 3a, even in the READY mode, the apparatus can disable the laser irradiation to thereby prevent execution of the laser irradiation caused due to erroneous operation by a third party or the operator himself.

In the above embodiment, the detection signal from the photo-sensor 57 is used to control the laser irradiation. Furthermore, the detection signal from the photo-sensor 57 may also be used for controlling turn-on/off of the aiming laser source 16 and the illumination light source 41. In this case, when the controller 60 receives no detection signal for a predetermined time after power-on of the apparatus or after receipt of the instruction of the aiming beam irradiation, the laser source 16 and the light source 41 are automatically turned off. Alternatively, when the detection signal stops generating during operation, the sources 16 and 41 are also automatically turned off after interruption of the laser irradiation. Then, the laser source 16 and the light source 41 are turned on at the time when the operator looks through the eyepieces 3a. In the above manner, unnecessary light-up of the laser source 16 and the light source 41 can be prevented, thus reducing burden on the patient, and achieving reduction of power consumption and increase of each life of the laser source 16 and the light source 41. Moreover, power sources (power supply) of the whole or part of the apparatus may be controlled in accordance with the detection signal from the photo-sensor 57.

Figure 3:
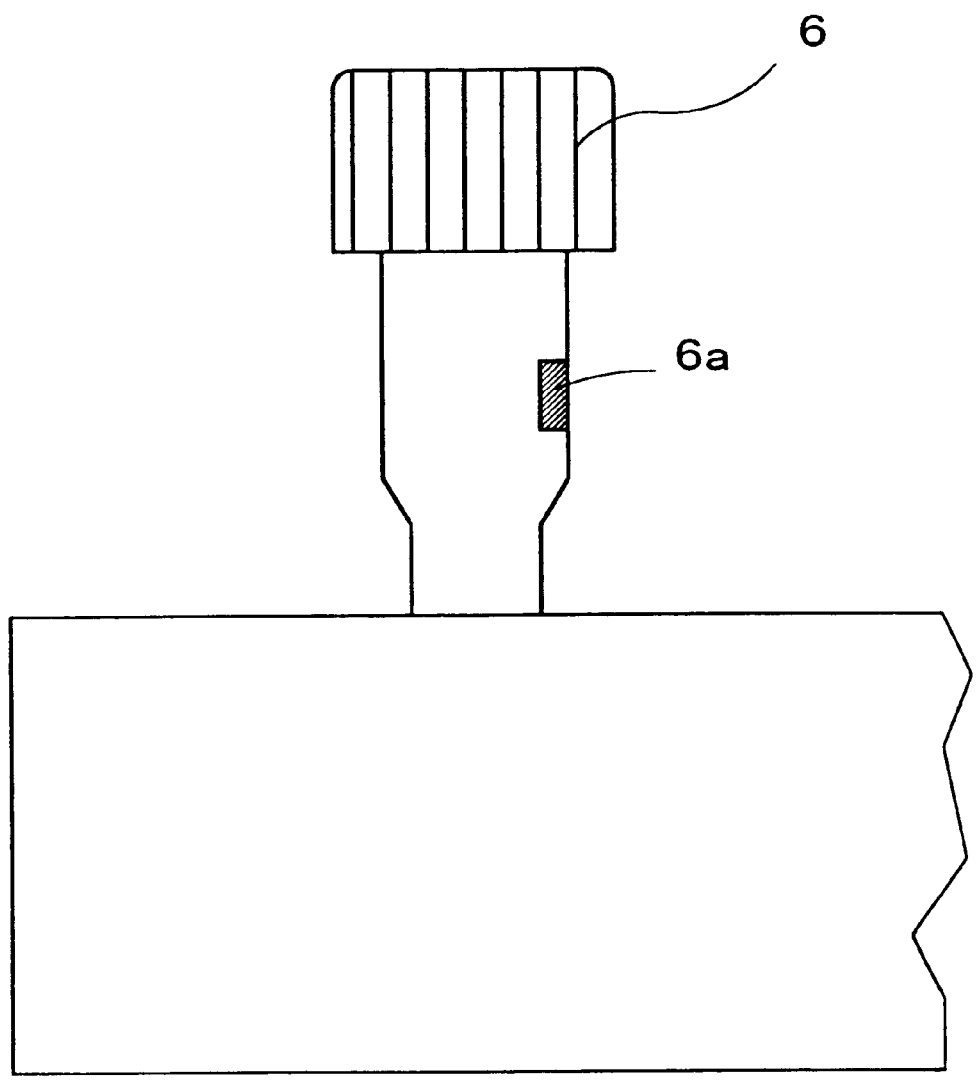
FIG. 3 is a schematic view of a joystick provided with a sensor.

The photo-sensor 57 is disposed in the eyepieces 3a in the above embodiment, it may be placed in any portion that the operator always uses in executing the laser irradiation. For example, as shown in FIG. 3, a sensor 6a may be provided in the joystick 6 used for alignment of the apparatus. In this case, the laser irradiation is disabled if the operator does not grip the joystick 6. Alternatively, a sensor may be disposed in a seat which the operator sits in.

In the above embodiment, the photo-sensor is used as a device for detecting whether the operator is in the predetermined condition with respect to the apparatus to enable the laser irradiation. Alternative design is the use of a touch sensor or a micro-switch.

Although the laser irradiation is disabled by the first shutter 14 placed in the optical path, it may be prohibited by the second shutter 18 or with control of the laser source 10 itself.

The laser irradiation instruction signal is input with the footswitch 5 in the above embodiment, but it may be input with a trigger switch if provided on the top of the joystick 6.

In the above embodiment, the laser treatment apparatus of the present invention is applied to the ophthalmic laser photocoagulation apparatus using the slit lamp. However, the present invention is not limited thereto and may be embodied in other specific forms without departing from the essential characteristics thereof.

Next, a second embodiment of the laser treatment apparatus according to the present invention will be explained, referring to FIG. 4. In this embodiment, the present invention is applied to a laser depilation apparatus.

Figure 4:
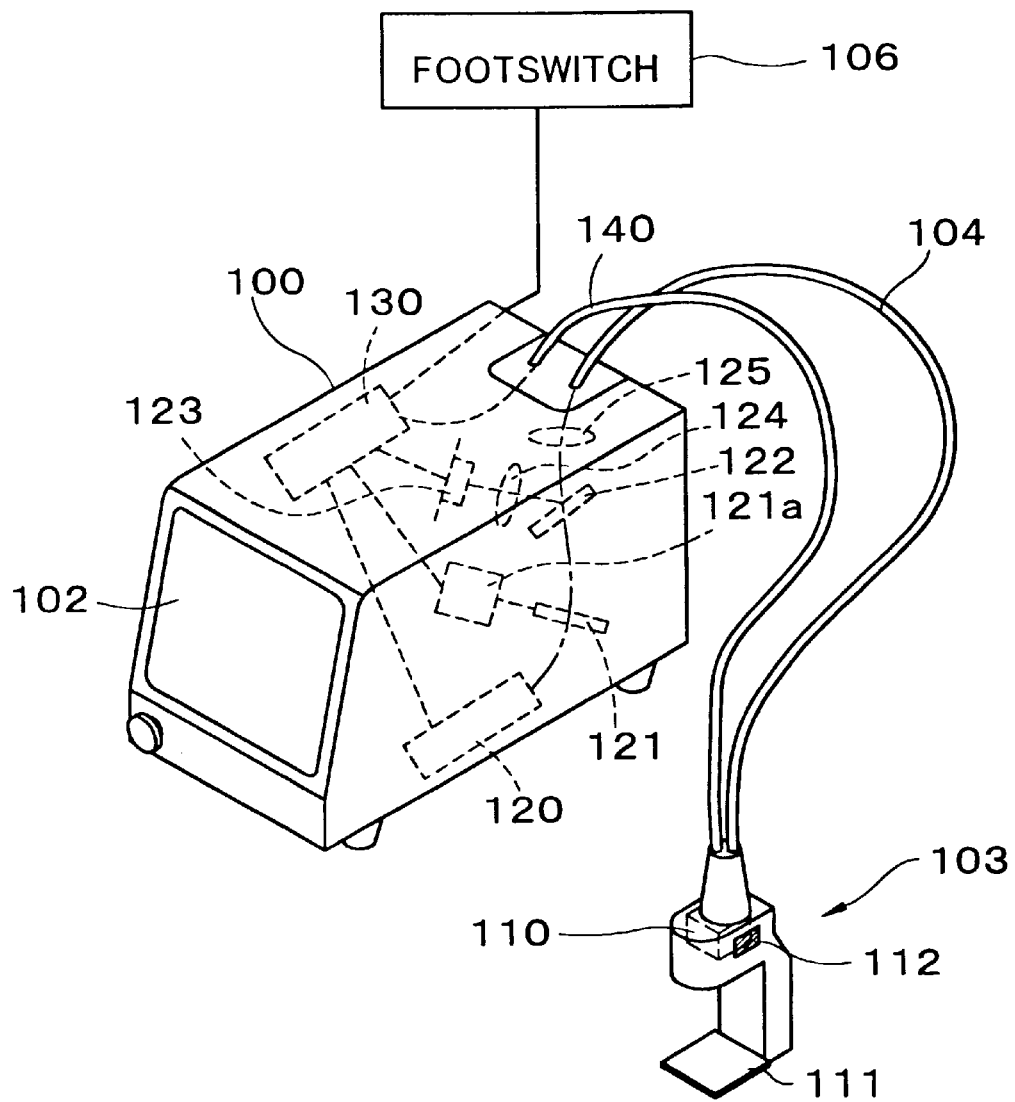
FIG. 4 is a perspective view of a laser depilation apparatus in a second embodiment according to the present invention.

In FIG. 4, the treatment beam emitted from a laser source 120 disposed in a main unit 100 of the laser depilation apparatus is delivered into a hand-piece 103 through a fiber 104. In the hand-piece 103 there is provided a part of an irradiation optical system 110 for causing the treatment beam to scan and irradiate an affected part of a patient. This part of the irradiation optical system 110 may be arranged only to irradiate the affected part without scanning. The hand-piece 103 is provided at its end with a glass plate 111. The laser irradiation is performed with the glass plate 111 made into contact with the skin of the patient. The hand-piece 103 is also provided with a touch sensor 102 disposed at a portion of the hand-piece 103 which is touched by an operator's hand when the operator holds the hand-piece 103 with his hand. This touch sensor 102 detects whether the operator is holding the hand-piece 103, in other words, whether the operator is in a predetermined condition to enable the laser irradiation.

Only if a READY mode is established with the touch of a key on a control panel (liquid crystal touch-panel) 102 and besides a detection signal from the touch sensor 112 is continuously input to a controller 130, an irradiation instruction signal from a footswitch 106 is determined to be effective. If the operator does not hold the hand-piece 103, the laser irradiation will not be performed even if the irradiation instruction signal is input in error.

In FIG. 4, numeral 121 is a safety shutter, numeral 121a is a shutter moving unit, numeral 122 is a dichroic mirror, numeral 123 is a laser source which emits an aiming beam, numeral 124 is a collimator lens, numeral 125 is a condensing lens, and numeral 140 is a communication cable for transmitting/receiving signals between the main unit 100 (the controller 130) and the hand-piece 103.

As described above, according to the present invention, erroneous irradiation of the treatment beam can be prevented, thereby reducing the power consumption of the apparatus.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A laser treatment apparatus for irradiating an affected part of a patient with a treatment laser irradiation beam to treat the affected part, the apparatus including:

treatment beam irradiation means including an irradiation optical system for delivering the treatment laser irradiation beam to the affected part to irradiate it;

trigger means for inputting a trigger signal of irradiation of the treatment laser irradiation beam;

mode selection means for selecting one of a ready mode in which the irradiation is enabled when the trigger signal is input and a standby mode in which the treatment laser irradiation beam is disabled even if the trigger signal is input;

detection means for detecting whether an operator is in a predetermined condition to enable the treatment laser irradiation beam;

illumination means, provided with an illumination light source which emits an illumination light, for illuminating an area including the affected part with the illumination light emitted from the illumination light source; and light source control means for controlling the illumination light source in accordance with a detection result by the detection means.

2. The laser treatment apparatus according to claim 1, further including observation means provided with eyepieces and an observation optical system for allowing the operator to observe the affected part, wherein the detection means is disposed in the eyepieces to detect whether the operator is in the predetermined condition to enable the treatment laser irradiation beam based on whether a face of the operator is within a predetermined distance from the eyepieces.

3. The laser treatment apparatus according to claim 2, wherein the detection means includes one of a photo-sensor, a touch-sensor, and a micro-switch.

4. The laser treatment apparatus according to claim 1, further including:

aiming beam irradiation means, provided with an aiming laser source which emits an aiming beam to be used for sighting the treatment laser beam on the affected part, for delivering the aiming beam emitted from the aiming laser source to the affected part to irradiate it, wherein the light source control means controls the aiming laser source in accordance with the detection result by the detection means.

5. The laser treatment apparatus according to claim 1, further including power source control means for controlling power supply to a whole or part of the apparatus in accordance with the detection result by the detection means.

6. A laser treatment apparatus for irradiating an affected part of a patient with a treatment laser irradiation beam to treat the affected part, the apparatus including:

treatment beam irradiation means including an irradiation optical system for delivering the treatment laser irradiation beam to the affected part to irradiate it;

trigger means for inputting a trigger signal of irradiation of the treatment laser irradiation beam;

mode selection means for selecting one of a ready mode in which the treatment laser irradiation beam is enabled when the trigger signal is input and a standby mode in which the treatment laser irradiation beam is disabled even if the trigger signal is input;

a moving mechanism provided with a hand operated member for moving at least a part of the irradiation optical system with respect to the affected part;

detection means disposed in the hand operated member to detect whether an operator is in a predetermined condition to enable the treatment laser irradiation beam based on whether the operator is holding the hand operated member; and irradiation control means for controlling the treatment laser irradiation beam in accordance with a selection result by the mode selection means, a detection result by the detection means, and input of the trigger signal.

7. The laser treatment apparatus according to claim 6, wherein the detection means includes one of a photo-sensor, a touch-sensor, and a micro-switch.

8. A laser treatment apparatus for irradiating an affected part of a patient with a treatment laser irradiation beam to treat the affected part, the apparatus including:

treatment beam irradiation means including an irradiation optical system for delivering the treatment laser irradiation beam to the affected part to irradiate it;

trigger means for inputting a trigger signal of irradiation of the treatment laser irradiation beam;

mode selection means for selecting one of a ready mode in which the treatment laser irradiation beam is enabled when the trigger signal is input and a standby mode in which the treatment laser irradiation beam is disabled even if the trigger signal is input;

a hand-piece in which at least a part of the irradiation optical system is disposed;

detection means disposed in the hand-piece to detect whether an operator is in a predetermined condition to enable the treatment laser irradiation beam based on whether the operator is holding the hand-piece; and irradiation control means for controlling the treatment laser irradiation beam in accordance with a selection result by the mode selection means, a detection result by the detection means, and input of the trigger signal.

9. The laser treatment apparatus according to claim 8, wherein the detection means includes one of a photo-sensor, a touch-sensor, and a micro-switch.

* * * * *